(12) United States Patent
Reynolds

(10) Patent No.: US 6,802,828 B2
(45) Date of Patent: Oct. 12, 2004

(54) SYSTEM FOR FILLING AND ASSEMBLING PHARMACEUTICAL DELIVERY DEVICES

(75) Inventor: David L. Reynolds, Bromont (CA)

(73) Assignee: Duoject Medical Systems, Inc., Bromont (CA)

( * ) Notice: Subject to any disclaimer, the term of this patent is extended or adjusted under 35 U.S.C. 154(b) by 0 days.

(21) Appl. No.: 09/993,299

(22) Filed: Nov. 23, 2001

(65) Prior Publication Data

US 2003/0100866 A1 May 29, 2003

(51) Int. Cl.[7] ............................ A61M 5/32; A61M 5/315
(52) U.S. Cl. ...................... 604/199; 604/218; 604/228
(58) Field of Search ................................ 604/187, 199, 604/218, 227, 228

(56) References Cited

U.S. PATENT DOCUMENTS

| | | | |
|---|---|---|---|
| 2,453,590 A | * 11/1948 | Poux | 604/201 |
| 2,860,635 A | * 11/1958 | Wilburn | 604/190 |
| 4,091,812 A | * 5/1978 | Helixon et al. | 604/208 |
| 4,886,495 A | 12/1989 | Reynolds | |
| 5,137,511 A | 8/1992 | Reynolds | |
| 5,364,369 A | 11/1994 | Reynolds | |
| 5,387,195 A | * 2/1995 | Hicks | 604/110 |
| 5,554,125 A | 9/1996 | Reynolds | |
| 6,004,299 A | * 12/1999 | Arai et al. | 604/218 |
| 6,149,623 A | 11/2000 | Reynolds | |
| 6,156,014 A | * 12/2000 | Petersen et al. | 604/218 |

FOREIGN PATENT DOCUMENTS

| | | |
|---|---|---|
| EP | 0298585 | 1/1989 |
| EP | 0 298 585 B1 | 10/1993 |
| GB | 2249727 A | 5/1992 |
| WO | PCT/JP94/02295 | 7/1995 |
| WO | PCT/US99/05449 | 9/1999 |
| WO | PCT/CA02/01772 | 11/2002 |

* cited by examiner

Primary Examiner—Anhtuan T. Nguyen
Assistant Examiner—Catherine S. Williams
(74) Attorney, Agent, or Firm—Woodling, Krost and Rust

(57) ABSTRACT

A system is provided which permits syringe barrels of prefilled disposable syringes to be filled and capped on standard vial filling equipment, and which permits the syringe body and piston comprising the barrel to be simultaneously sterilized by a sterilizing gas. The system provides means for stabilizing syringe barrels so they can be conveyed upright on their bases without tipping through vial filling and capping equipment. Preferably, the stabilizing means comprises a cylindrical sleeve into which the lower end of the syringe body is inserted, thereby stably supporting it against tipping. The system also provides means by which the piston is retained in close proximity to the lower end of the syringe body, but slightly separated therefrom to permit access to all surfaces of the piston by a sterilizing gas. Preferably, the piston is retained directly below the lower end of the syringe body, and substantially centred therewith, to permit the piston to be inserted into the lower end of the body merely by pushing the body and piston together.

15 Claims, 13 Drawing Sheets

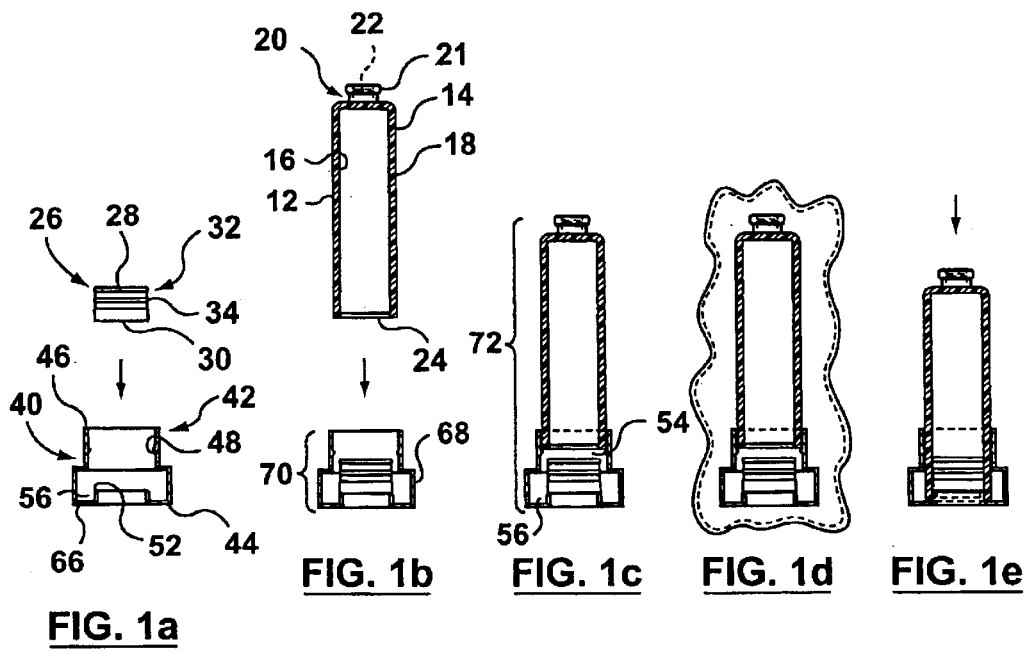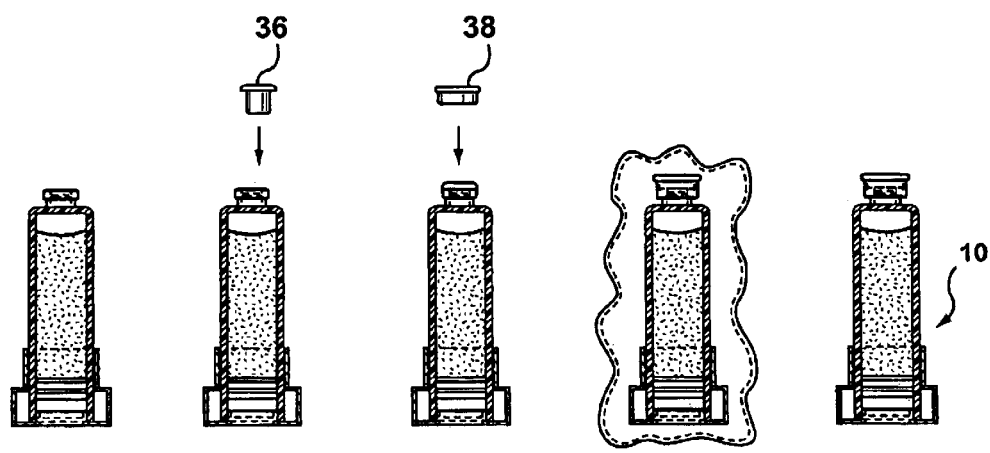

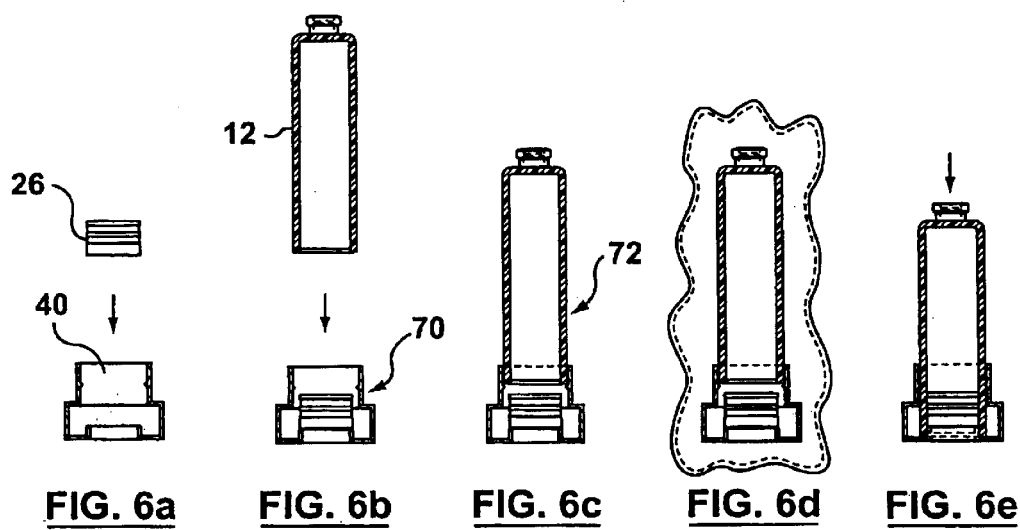
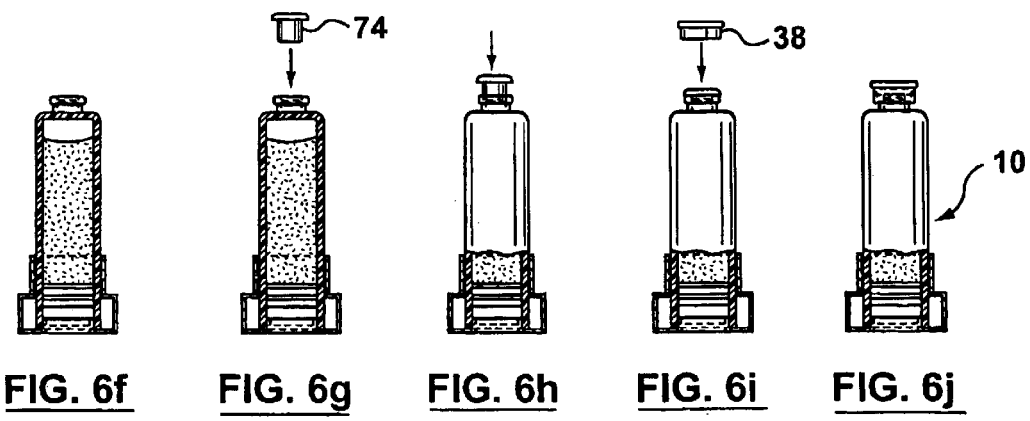

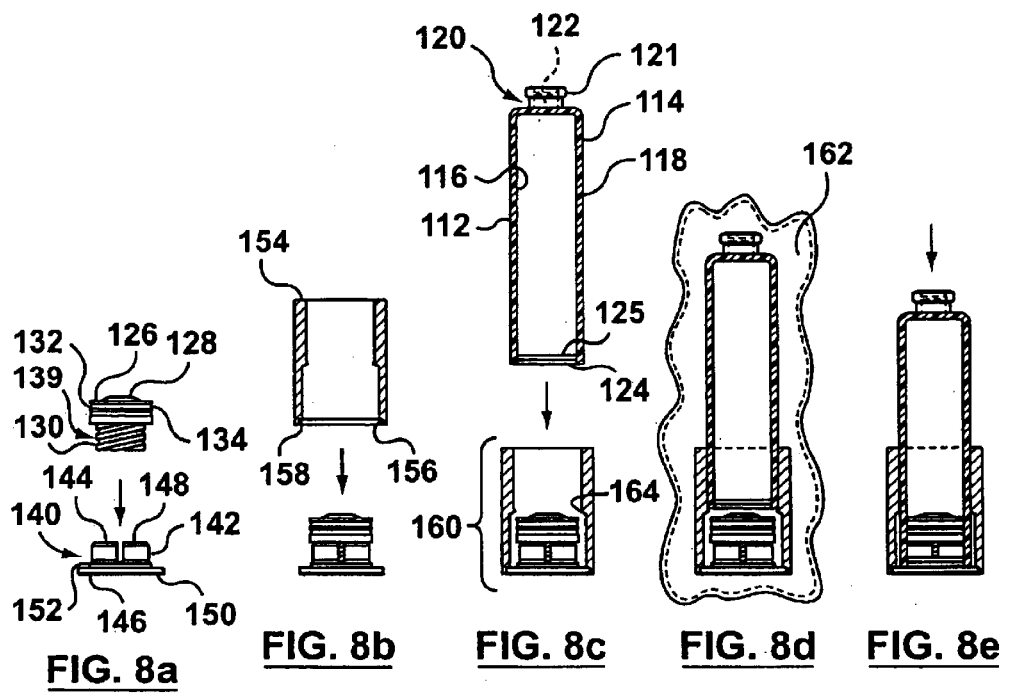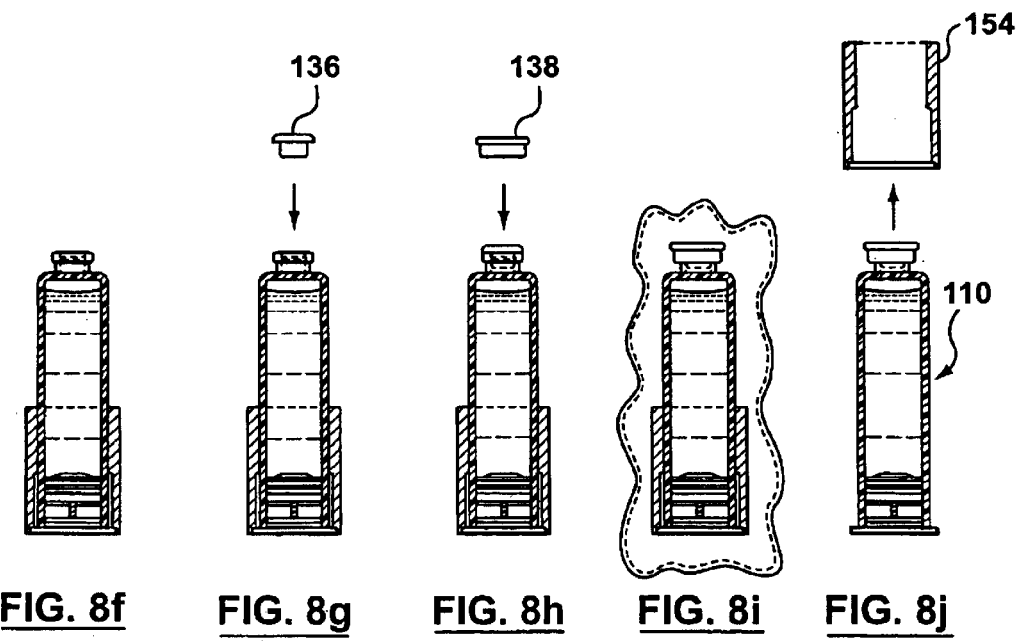

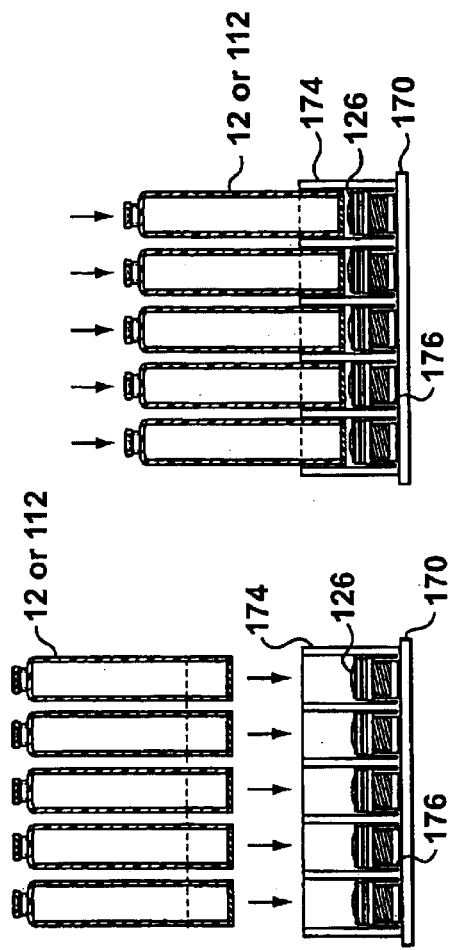
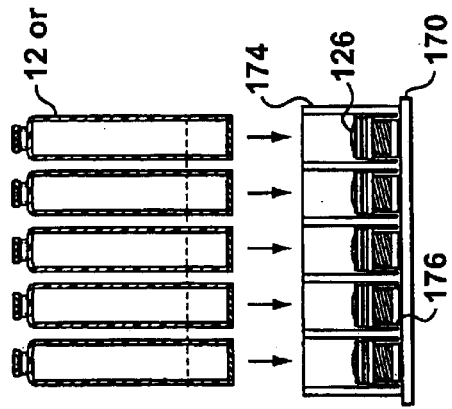
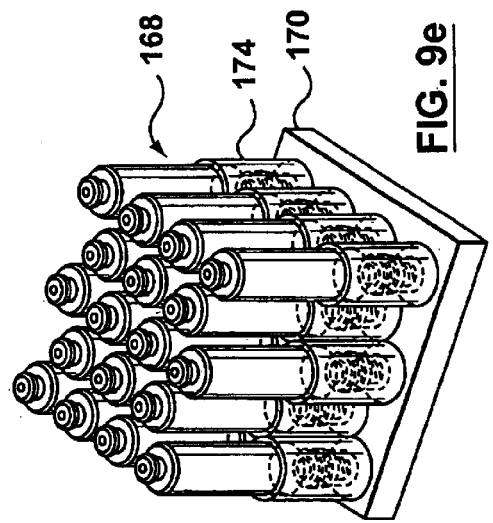
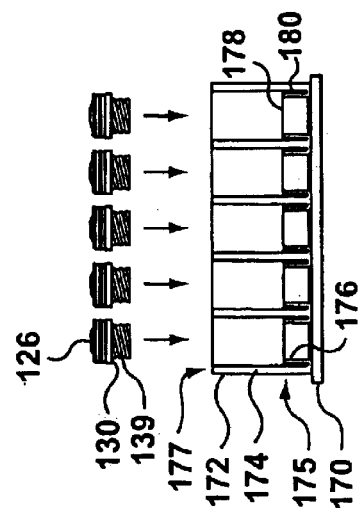
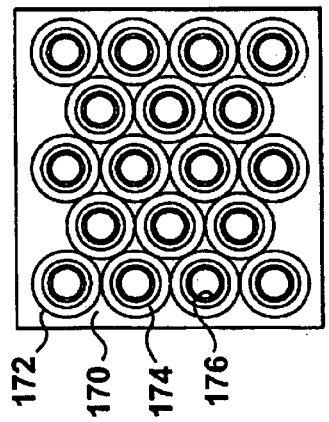

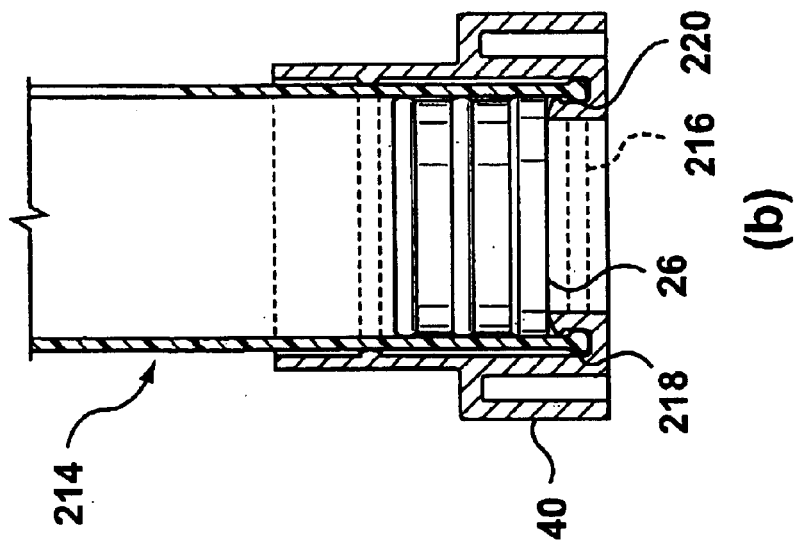
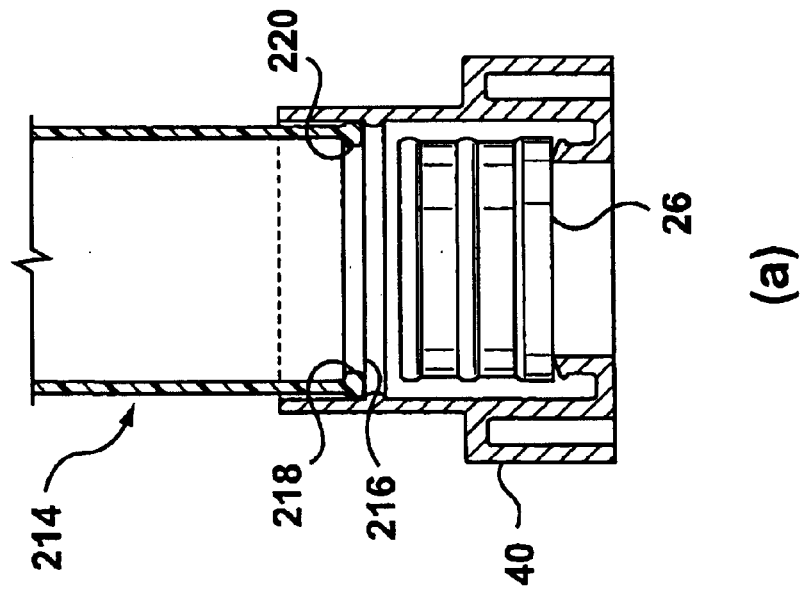
FIG. 14

SYSTEM FOR FILLING AND ASSEMBLING PHARMACEUTICAL DELIVERY DEVICES

FIELD OF THE INVENTION

The invention relates to the production of prefilled syringes for use in medical or veterinary treatment.

BACKGROUND OF THE INVENTION

Prefilled disposable syringes have gained wide acceptance as a preferred dosage form for administration of medicaments, primarily for reasons of safety and convenience. Most importantly, prefilled syringes minimize handling of a medicament prior to administration, thereby reducing the chance of dosage errors or contamination of the medicament.

Many different types of prefilled disposable syringes have been developed. Most known prefilled syringes include an elongate syringe "cartridge" or "barrel" comprising a cylindrical glass or plastic container into which the medicament or a component thereof is prefilled. In some types of prefilled syringe, the barrel forms the body of a syringe, having a mouth which permits attachment to an injection needle, and a movable bottom comprising an elastomeric piston which is acted upon by a plunger to administer the medicament.

One common problem with prefilled disposable syringes is that a dedicated filling and capping line is usually required to fill the medicament into the syringe barrel. This problem has previously been addressed by the invention described in the applicant's European Patent No. 298,585, which describes a system for producing prefilled syringe barrels on ordinary equipment for filling and capping pharmaceutical vials This patent describes a system whereby the syringe barrel is made shorter and wider than a conventional barrel, so that it has the shape of a standard pharmaceutical vial, and is then filled and capped on standard machinery for filling and capping vials, through which the barrels are conveyed while standing on their bases. Since the pharmaceutical vial is a standardized container which is widely used in the pharmaceutical industry, most pharmaceutical companies have existing vial filling equipment. The equipment need only be modified by the addition of a station for insertion of the rubber piston into the body of the barrel. Therefore, the invention described in the applicant's prior patent eliminates the need for specialized filling equipment, thereby reducing cost.

Despite the improvements described in the applicant's above-mentioned European patent, the further disadvantage exists that the relatively squat vial-shaped barrels cannot be used in all types of delivery systems. Some delivery systems, such as syringe pumps and two component systems, may require the use of conventional, elongate barrels which cannot be filled on standard vial-filling equipment. Therefore, it would be advantageous to provide a system which allows the preparation of conventional, elongate prefilled syringe barrels on standard equipment for filling and capping pharmaceutical vials.

A further disadvantage exists in that it is not possible to adequately sterilize the assembled syringe barrel (i.e. with the piston completely inserted in the body) by conventional sterilizing agents, including gamma radiation and sterilizing gases such as ethylene oxide or steam. While gamma radiation would sterilize the assembled barrel, it destroys the elasticity of the rubber and therefore cannot be used. Sterilizing gases cannot adequately contact all surfaces of the piston once it is inserted in the body and therefore cannot be used. It would be desirable to supply a syringe barrel which is at least partially assembled and preferably pre-sterilized so as to allow maximum flexibility during the filling operation.

SUMMARY OF THE INVENTION

The above-mentioned disadvantages of the prior art are overcome by the present invention, which provides a system for filling and assembling pharmaceutical delivery devices capable of accommodating barrels of various dimensions including elongate syringe barrels. The system according to the invention also provides for partial pre-assembly of the body and the piston, thereby permitting simultaneous sterilization of the body and piston by a sterilizing gas.

In the system according to the invention, means are provided for stabilizing syringe barrels such that they can be conveyed upright without tipping through equipment for filling and capping pharmaceutical vials. Preferably, the stabilizing means comprises a cylindrical sleeve into which the rimmed end of the body (i.e. the end which receives the piston) is inserted, thereby stably supporting the body against tipping.

The system according to the invention also provides means by which the piston is retained in close proximity to the rimmed end of the body, but slightly separated therefrom to permit access to all surfaces of the piston by a sterilizing gas. Preferably, the piston is retained directly below the rimmed end of the body, and substantially centred therewith, to permit the piston to be inserted into the rimmed end of the body merely by pushing the body and piston together.

Accordingly, in one aspect, the present invention provides An assembly for forming a barrel of a pre-filled syringe, comprising: (a) a syringe body having a generally cylindrical side wall with an inner surface and an outersurface, the sidewall extending between a neck end and a rimmed end; (b) a generally cylindrical elastomeric piston having an upper surface, a side surface adapted to form a hermetic seal with the inner surface of the cylindrical side wall when inserted into the open rimmed end of the syringe body, and a lower surface opposite the upper surface; (c) a generally cylindrical sleeve having a base end and a top end, wherein said syringe body is received inside the top end of the sleeve in a close fit with the rimmed end of the syringe body located intermediate the top end and the base end of the sleeve; and (d) piston support means in contact with the sleeve, said piston support means having a support surface on which the piston is supported with its upper surface spaced from the rimmed end of the syringe body and substantially concentric therewith, such that a gap exists between the upper surface of the piston and the rimmed end of the syringe body, thereby permitting sterilization of the syringe body and the piston by a sterilizing gas.

In another aspect, the present invention provides a method for producing a pre-filled syringe body for a pre-filled syringe, the syringe body comprising a barrel and a piston, the barrel having a generally cylindrical side wall with an inner surface and an outer surface, the side wall extending between a neck end and a rimmed end of the barrel, the piston being generally cylindrical and formed of an elastomeric material with an upper surface, a side surface adapted to form a hermetic seal with the inner surface of the barrel when inserted into the open rimmed end of the barrel, and a lower surface opposite the upper surface, the method comprising: (a) forming a first assembly comprising said elastomeric piston, a generally cylindrical sleeve having an inner surface, and outer surface, a base end and a top end, and piston support means in contact with the sleeve and having a piston support surface on which the piston is supported with its lower surface engaging the piston support surface, the piston support surface being spaced radially inwardly of the inner surface of the sleeve; (b) forming a second assembly by inserting the rimmed end of the barrel into the top end of the sleeve to a sufficient depth that the barrel is stably supported in the sleeve, and such that the rimmed end is located intermediate the top end and the base end of the sleeve with a gap between the upper surface of the piston and the rimmed end of the barrel; (c) sterilizing the second assembly with a sterilizing gas; (d) applying a force to the second assembly to cause relative movement of the barrel toward the base end of the sleeve, causing insertion of the piston into the barrel such that the side surface of the piston forms a hermetic seal with the inner surface of the barrel and seals the rimmed end of the barrel; (e) filling said barrel with a medicament or a component thereof through the neck end using equipment for filling and capping pharmaceutical vials; and (f) capping the neck end of the barrel using said equipment for filling and capping pharmaceutical vials; wherein, subsequent to insertion of the piston in step (d), said second assembly is conveyed through at least a portion of said equipment for filling and capping pharmaceutical vials while freestanding in an upright position.

BRIEF DESCRIPTION OF THE DRAWINGS

The invention will now be described, by way of example only, by reference to the accompanying drawings in which:

FIG. 1 schematically illustrates a method for preparing a prefilled syringe barrel according to a first preferred embodiment of the present invention;

FIG. 6 schematically illustrates a variant of the method shown in FIG. 1 in which the body is filled with a freeze-dried medicament;

FIG. 8 schematically illustrates a method for preparing a prefilled syringe barrel according to a second preferred embodiment of the present invention;

FIG. 9 schematically illustrates a variant of the second preferred embodiment in which a plurality of piston supports and sleeves are secured to a handling tray;

FIG. 14 illustrates a variant of the syringe barrel according to the first preferred embodiment of the present invention.

DETAILED DESCRIPTION OF PREFERRED EMBODIMENTS

Figure 2:
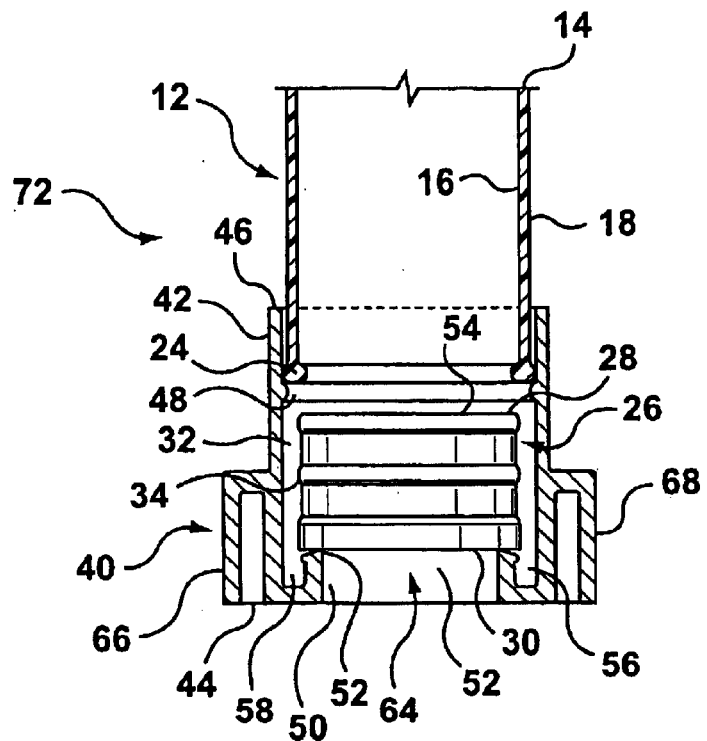
FIG. 2 illustrates the lower portion of the syringe barrel of FIG. 1 prior to insertion of the piston into the body.

A first preferred embodiment of the invention will now be discussed below in the context of a syringe barrel which is intended for use in a delivery device for a two component medicament. Such a delivery device is described in U.S. Pat. No. 6,149,623, issued on Nov. 21, 2000 and co-owned by the applicant of the present application, which is incorporated herein by reference in its entirety.

FIG. 1 illustrates a preferred sequence of steps to be followed during preparation of a prefilled syringe barrel 10 for use in a two component delivery device. The illustrations of the syringe barrel shown in FIG. 1 are somewhat schematic. Details of the lower portions of the syringe barrel 10 are more clearly shown in FIGS. 2 and 3.

The barrel 10 comprises a body 12 preferably made of glass and having a generally cylindrical side wall 14 with an inner surface 16 and an outer surface 18. At one end, the body 12 has a relatively narrow neck 20 with a neck flange 21 surrounding an open mouth 22, and at the other end the body 12 has an open rimmed end 24. Although the lower end of the body 12 is referred to herein as the "rimmed end", it is to be appreciated that the body 12 may or may not have a perceptible inwardly or outwardly extending rim at its lower edge.

The body 12 illustrated in FIG. 1 has a height to base ratio of approximately 4.5:1. It will be appreciated that the present invention can be utilized with barrels of various dimensions, including barrels having greater height to base ratios than that shown in FIG. 1, and barrels having lower height to base ratios, such as the vial-shaped barrels described above which generally have height to base ratios not exceeding 2.5:1.

Barrel 10 further comprises a generally cylindrical elastomeric piston 26 having an upper surface 28 which forms the bottom wall of the barrel 10 in its assembled state, and an opposed lower surface 30 with an internally threaded bore (not shown). Piston 26 also has a side surface 32 connecting the upper and lower surfaces 28 and 30, the side surface 32 being adapted to form a hermetic seal with the inner surface 16 of body 12, and preferably being provided with one or more ribs 34 to improve the seal with the body 12. Piston 26 is preferably made from an elastomeric material such as rubber.

The open neck 20 of body 12 is sealed in a conventional manner by an elastomeric closure 36 with an overlying metal cap 38 crimped over the neck flange 21.

Figure 3:
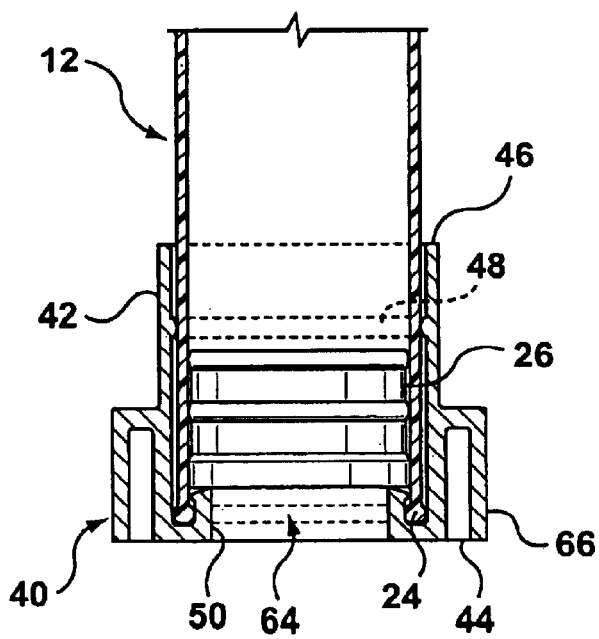
FIG. 3 illustrates the lower portion of the syringe barrel of FIG. 1 after insertion of the piston into the body.
Figure 4E:
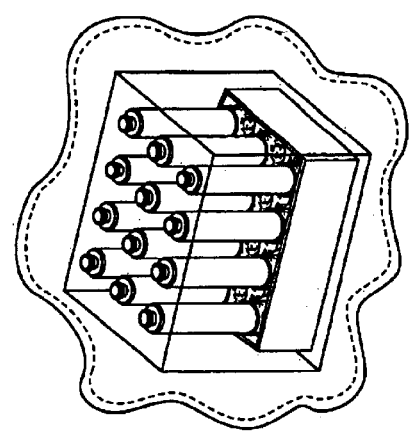
FIG. 4 schematically illustrates a variant of the method shown in FIG. 1 in which the syringe barrels are packaged in trays for sterilization.
Figure 4K:
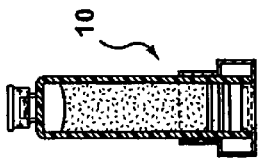
Figure 4D:
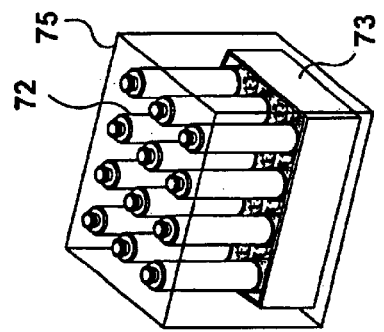
Figure 4J:
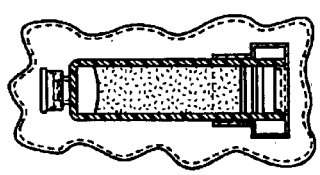
Figure 4I:
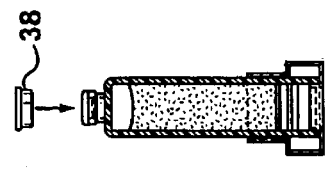
Figure 4C:
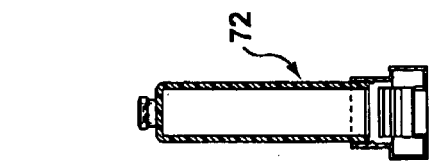
Figure 4H:
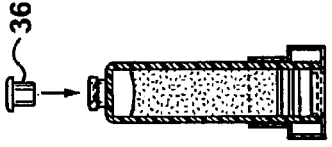
Figure 4G:
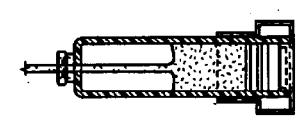
Figure 4B:
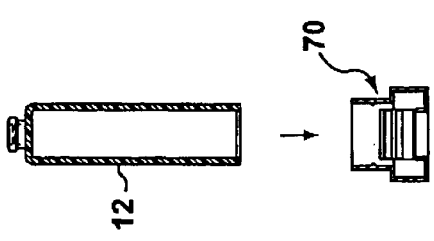
Figure 4A:
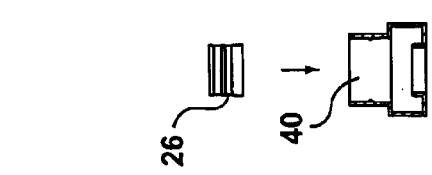
Figure 4F:
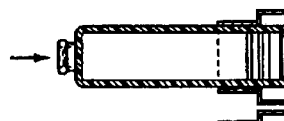

Barrel 10 is also provided with an activation cap 40 at its rimmed end 24, the cap 40 performing a number of functions which are described below. As best seen in FIGS. 2 and 3, activation cap 40 comprises a generally cylindrical sleeve 42 having a base end 44 and a top end 46, the rimmed end 24 of body 12 being received inside the top end 46 of sleeve 42 in a close fit with the rimmed end 24 being located intermediate the top end 46 and the base end 44 of the sleeve 42.

Preferably, the sleeve 42 has an inwardly projecting portion 48 extending radially inwardly from the inner wall of the sleeve 42 The inwardly projecting portion 48 shown in FIG. 1 comprises a detent of sufficient shape and size to retain the rimmed end 24 of the syringe body 12 intermediate the top end 46 and the base end 44 of the sleeve 42 in the absence of a force which pushes the rimmed end 24 of the body 12 and the base end 44 of the sleeve 42 toward one another, but which permits the rimmed end 24 to be pushed toward the base end 44 in response to a predetermined force, such as a downward force applied to the body 12 when the barrel 10 is standing upright on the base end 44 of the sleeve 42. As defined herein, a detent includes any inward projection of the sleeve 42 which is effective to retain the rimmed end 24 of the body 12, including a continuous circumferential lip or one or more protrusions, as shown in FIGS. 1 to 3, on the inner surface of the sleeve 42.

The activation cap 40 further comprises piston support means 50 including a piston support surface 52 on which the piston 26 is supported such that its upper surface 28 is spaced from the rimmed end 24 of the body 12, thereby providing a gap 54 between the piston and the body 12 which permits exposure of substantially the entire piston 26 and body 12 to a sterilizing gas as discussed below in greater detail Furthermore, the piston 26 is supported such that it is substantially concentric with the rimmed end 24 of the body 12, ready for insertion into the rimmed end 24.

In the preferred embodiment of FIG. 1, the piston support means 50 is in contact with the sleeve 42 and is integrally formed therewith, both being components of the activation cap 40. As shown in FIG. 1, the piston support surface 52 is positioned radially inwardly of the inner surface of the sleeve 42. Preferably, the piston support surface 52 is spaced inwardly from the inner surface of the sleeve 42 by a distance which is substantially equal to the thickness of the body side wall, thereby forming an annular recess 56 between the piston support surface 52 and the inner surface of the sleeve 42 The annular recess 56 has a bottom wall 58 connecting the piston support means 50 and the sleeve 42 and located intermediate the piston support surface 52 and the lower surface of the base end 44 of the sleeve 42, such that when a predetermined force is applied to push the rimmed end 24 of the body 12 into the annular recess 56 until the rimmed end 24 engages the bottom wall 58, the piston 26 becomes fully inserted in the body 24 with its side surface 32 forming a hermetic seal with the inner surface 16 of the body 12.

In order to permit engagement of piston 26 by a plunger, the piston support surface 52 is annular with a central aperture 64, and engages an outer edge of the lower surface 30 of the piston 26. In the embodiment illustrated in FIGS. 1 to 3, the piston is preferably provided with a threaded bore (not shown) open to its lower surface 30 which is adapted for connection to the threaded end of a plunger (shown in FIG. 4)

As discussed above, the system of the invention is adapted to improve the stability of conventional, elongate syringe barrels, thereby permitting them to be conveyed standing upright through standard equipment for filling and capping pharmaceutical vials. This object is partly attained by provision of the sleeve 42, which may lower the centre of gravity of the barrel 10 somewhat, thereby improving its stability. Stability can be further enhanced by increasing the thickness of the sleeve 42 throughout part or all of its height For example, as shown in FIG. 1, the sleeve 42 may preferably be provided with an outwardly projecting flange 66 at its base end 44. The flange 66 has a diameter and a height so as to prevent interference such as would cause tipping when the barrel 10 is conveyed standing upright on the base end 44 through standard equipment for filling and capping pharmaceutical vials. Such interference typically comprises a phenomenon known as "shingling", in which the flange of one barrel rides up over the flange of another barrel, resulting in tipping.

Shingling can be prevented as shown in the preferred embodiment of FIG. 1, in which the flange 66 has a substantially flat radially outwardly facing wall sufficient height that the flanges 66 of adjacent 10 will not ride up over one another.

FIG. 1 illustrates the steps involved in assembling and filling a barrel 10 with a liquid component of a medicament, which may comprise an active ingredient or a diluent to be combined with an active ingredient prior to administration.

The first step of the method, illustrated In FIG. 1a, comprises the formation of a first assembly 70 by inserting the piston 26 inside the sleeve 42 of activation cap 40 such that the lower surface 30 of piston 26 engages the piston support surface 52.

In the second step illustrated in FIG. 1b, a second assembly 72 is formed by inserting the rimmed end 24 of body 12 into the top end 46 of sleeve 42 to a sufficient depth that the body 12 is stably supported in the sleeve 42, and so that the rimmed end 24 is located intermediate the top end 46 and the base end 44 of the sleeve and gap 54 being formed between the upper surface 28 of piston 26 and the rimmed end 24 of the body 12, thereby permitting sterilization of the body 12, piston 26 and activation cap 40 by a sterilizing gas. A close-up cross-sectional view of the lower portion of second assembly 72 is shown in FIG. 2.

The next step in the method, schematically illustrated in FIG. 1d, comprises sterilization of the second assembly 72 by a sterilizing gas such as steam or ethylene oxide. FIG. 4 schematically illustrates a variant of the method of claim 1 in which the sterilization is performed while a plurality of assemblies 72 are packaged in trays 73 and covered with a plastic overwrap 75 so as to maintain sterility and keep them in place. A preferred plastic overwrap is sold under the trade-mark TYVEK™, which maintains sterility while allowing penetration of sterilizing gases such as ethylene oxide.

After sterilization, a force is applied to the second assembly 72 to cause relative movement of the body 12 toward the base end 44 of the sleeve 42, thereby causing insertion of the piston 26 into the body 12 such that the side surface 32 of the piston 26 forms a hermetic seal with the inner surface 16 of the body 12 and seals the rimmed end 24. Preferably, the body 12 is pushed downward into sleeve 42 in the direction shown by the arrow in FIG. 1d. This step may be performed while the assemblies 72 are packaged in trays 73 and covered with the overwrap 75. Alternatively, the overwrap 75 may preferably be removed from the sterile assemblies 72 (preferably in a sterile environment) prior to pushing the body 12 into sleeve 42, and the assemblies 72 may preferably also be removed from the tray 73 prior to performing this step.

With the piston 26 fully inserted in the body 12 as shown in FIG. 1e, and shown in greater detail in FIG. 3, the body 12 is now ready to be filled with a medicament, or a component thereof In this embodiment, the medicament is a liquid which is filled into the open mouth 22 of the body 12. As discussed above, the body 12 is filled on standard equipment for filling and capping pharmaceutical vials, and is conveyed through at least part of said equipment free-standing on the base end 44 of sleeve 42. The filled body 12 is illustrated in FIG. 1f.

The mouth 22 of the body 12 is then sealed in a conventional manner by application of an elastomeric closure 36 as shown in FIG. 1g, followed by application of a metal cap 38 over the closure 36 as shown in FIG. 1h, the cap 38 preferably being crimped over the neck flange 21 of the body 12. This is also the most common method for sealing standard pharmaceutical vials and is therefore easily performed on standard equipment for filling and capping pharmaceutical vials.

The next step in the method is illustrated in FIG. 1i and comprises an optional terminal sterilization step, in which the sealed barrel 10 is subjected to sterilization, for example by exposure to high temperatures in an autoclave. This step is also part of the normal vial filling process and is performed on standard equipment for filling and capping pharmaceutical vials.

As mentioned above, the barrel 10 of the first preferred embodiment comprises an activation and is therefore specifically directed to delivery devices for two component pharmaceuticals In the example described above, a liquid medicament, or a liquid component of a medicament, is contained in the barrel 10. However, the first preferred embodiment is also adaptable to the situation where the barrel 10 contains a solid medicament or a solid component of a medicament, which is to be combined with a liquid, such as a diluent, prior to administration.

Figures 5A, 5B, 5C, 5D, 5E:
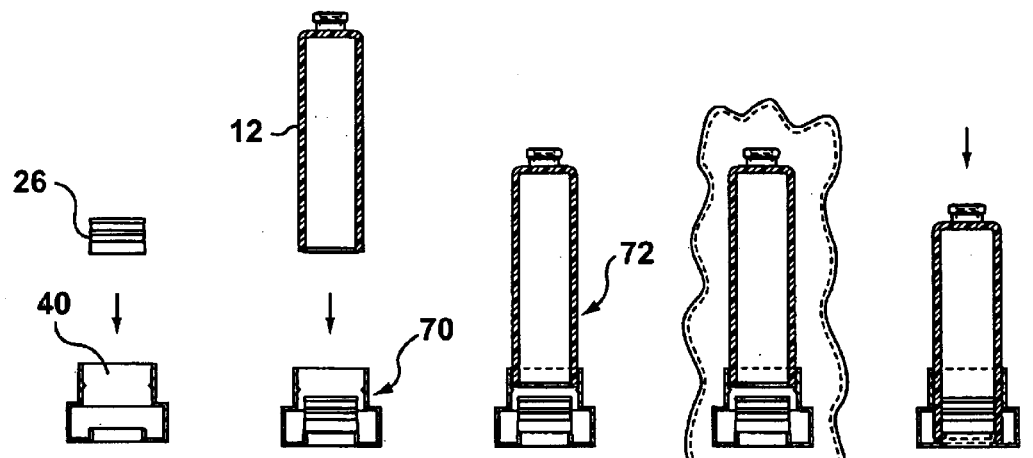
FIG. 5 schematically illustrates a variant of the method shown in FIG. 1 in which the body is filled with a powder.
Figures 5F, 5G, 5H, 5I:
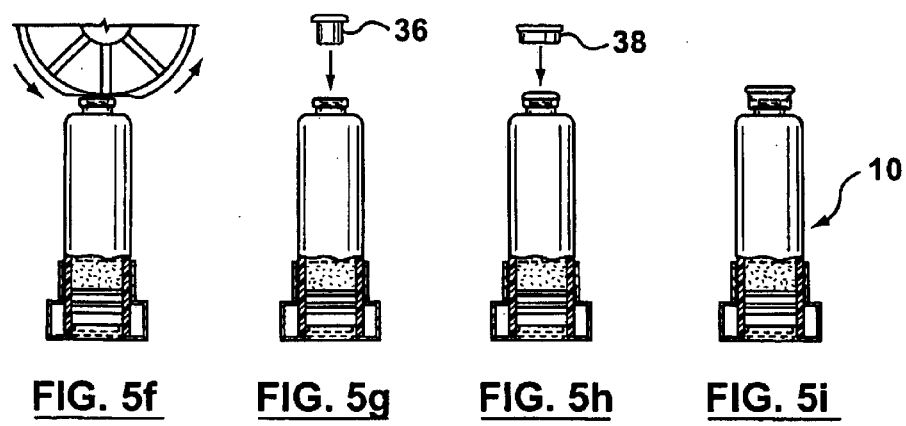

A first preferred method for filling barrel 10 with a solid medicament is illustrated in FIG. 5. The steps followed in FIG. 5 are preferably the same as those described above with reference to FIG. 1, with the exception of step 5f, in which a powdered substance is filled into body 12 through the mouth 22. Powder filling is also performed on standard equipment for filling and capping pharmaceutical vials.

A second preferred method for filling barrel 10 with a solid medicament is illustrated in FIG. 6. FIGS. 6a to 6e show preparation of the second assembly 72, followed by sterilization and seating of the piston 26 in the barrel body 10. These steps are identical to the steps followed in FIGS. 1a to 1e, discussed above. Next, the body is filled in FIG. 6f with a liquid composition containing a medicament or a component thereof. This step is identical to that shown in FIG. 1f. Next, a lyophilization stopper 74, comprising a vented elastomeric closure, is partially inserted into the neck 20 of body 12 such that a vent space 76 is formed. The liquid contents of the body 12 are then lyophilized as shown in FIG. 6g such that only a solid remains in the body 12. The stopper 74 is then completely inserted into neck 20 to close vent space 76 and seal the body, and a metal cap 38 is applied as in FIG. 1h. Although not shown in FIG. 6, the sealed barrel may be subjected to terminal sterilization. The steps shown in FIGS. 6f to 6i are performed on standard equipment for filling, lyophilizing and capping pharmaceutical vials.

Figures 7A, 7B:
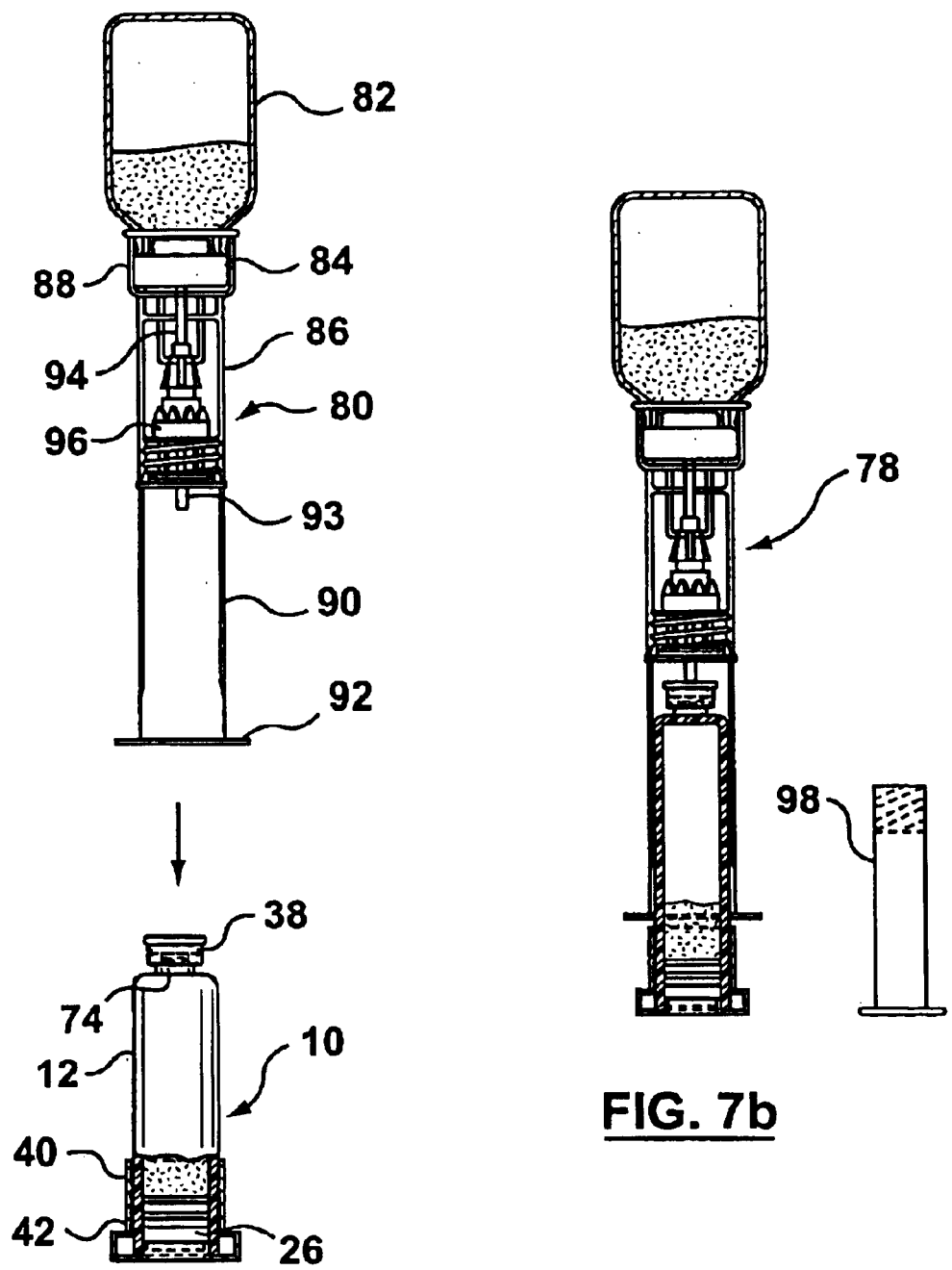
FIG. 7 illustrates combination of the syringe barrel of the first preferred embodiment with other components to form a delivery device for a two component medicament.
Figure 10E:
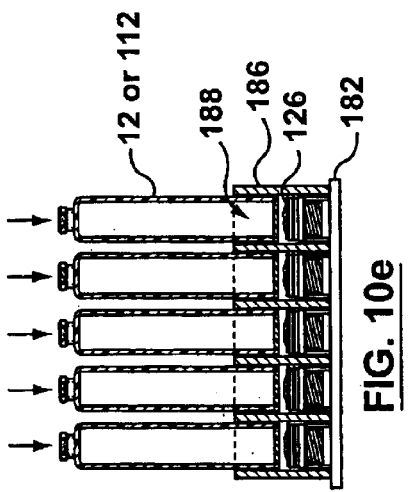
FIG. 10 schematically illustrates another variant of the second preferred embodiment in which a plurality of piston supports are secured to a handling tray.
Figure 10F:
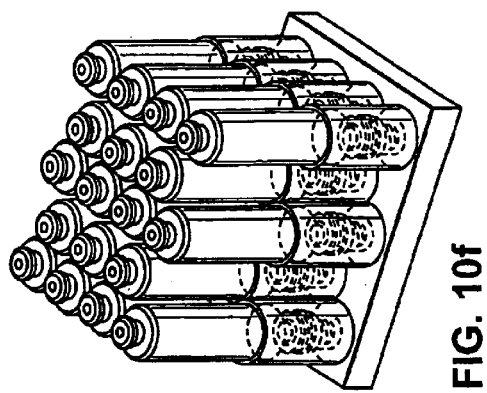
Figure 10D:
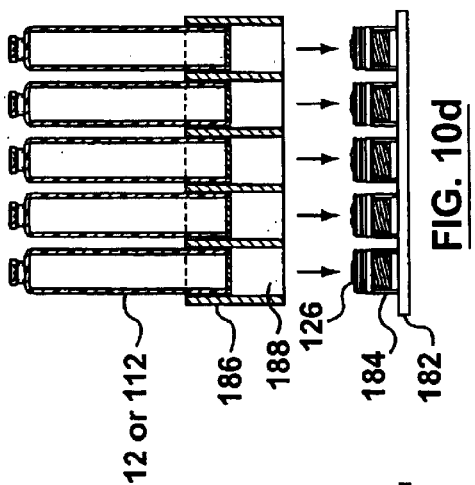
Figure 10C:
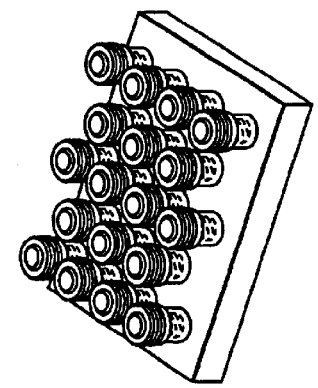
Figure 10B:
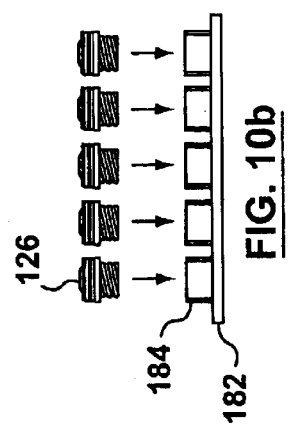
Figure 10A:
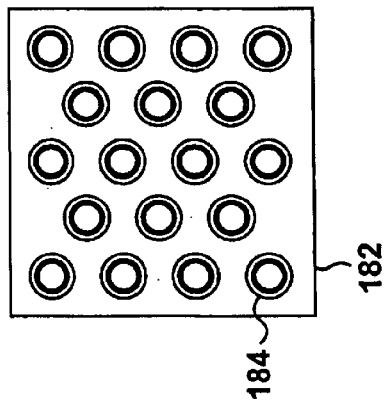

As mentioned above, the barrel 10 according to the first preferred embodiment is specifically adapted for use in a two component delivery device, such as preferred delivery device 78 shown in FIG. 7b. In order to assemble delivery device 78, the barrel 10 is combined with a pre-assembly 80 of the type illustrated in FIG. 7a, comprising a standard pharmaceutical vial 82 having a sealed neck 84, a vial coupling 86 with a vial socket 88 into which the neck 84 of vial 82 is received, and a syringe socket 90 with a finger flange 91 into which the barrel 10 is received.

The pre-assembly further comprises a rear needle 93 and a forward needle 94 housed in a luer lock assembly 96 which is secured to both the vial coupling 86 and the syringe socket 90. When the delivery device 78 is assembled as in FIG. 7b with the finger flange 91 engaging the top end 46 of activation cap 40, the ends of needles 93 and 94 do not penetrate the elastomeric closures of either the vial 82 or the barrel 10. The device 78 is activated by pushing the syringe socket 90 and the activation cap 40 together such that the sleeve 42 of the cap 40 becomes received inside syringe socket 90. The socket 90 and cap 40 are pushed together until the finger flange 91 engages the flange 66 of activation cap 40, at which point the ends of needles 93 and 94 penetrate the closures of the barrel 10 and the vial 82 respectively, allowing mixing of the respective contents of the vial 82 and barrel 10, in this example by attaching plunger 98 to the piston 26 and aspirating the liquid contents of the vial 82 into the barrel 10. The vial coupling 86 is then unthreaded from the luer 96, also removing the forward needle 94. An injection needle (not shown) is then threaded onto the exposed luer 96 to provide a complete prefilled disposable syringe (not shown). The components of pre-assembly 80, and the method for combining barrel 10 and pre-assembly 80 are described in greater detail in above-mentioned U.S. Pat. No. 6,149,623, which is incorporated herein by reference in its entirety. It will be appreciated that the activation cap 40 described herein functions in a manner similar to the driver described in the above-mentioned U.S. patent and identified by reference numeral 21 in FIGS. 17 and 18 thereof.

Where the barrel 10 contains a liquid medicament or a component thereof, the vial 82 of pre-assembly 80 may comprise either a solid or a liquid. Where the vial 82 contains a solid, the medicament is formed by pushing the liquid contents of barrel 10 into the vial 82, mixing the solid and liquid ingredients, followed by aspiration of the medicament suspension or solution into the barrel 10 prior to removal of the vial coupling 86.

Figure 13:
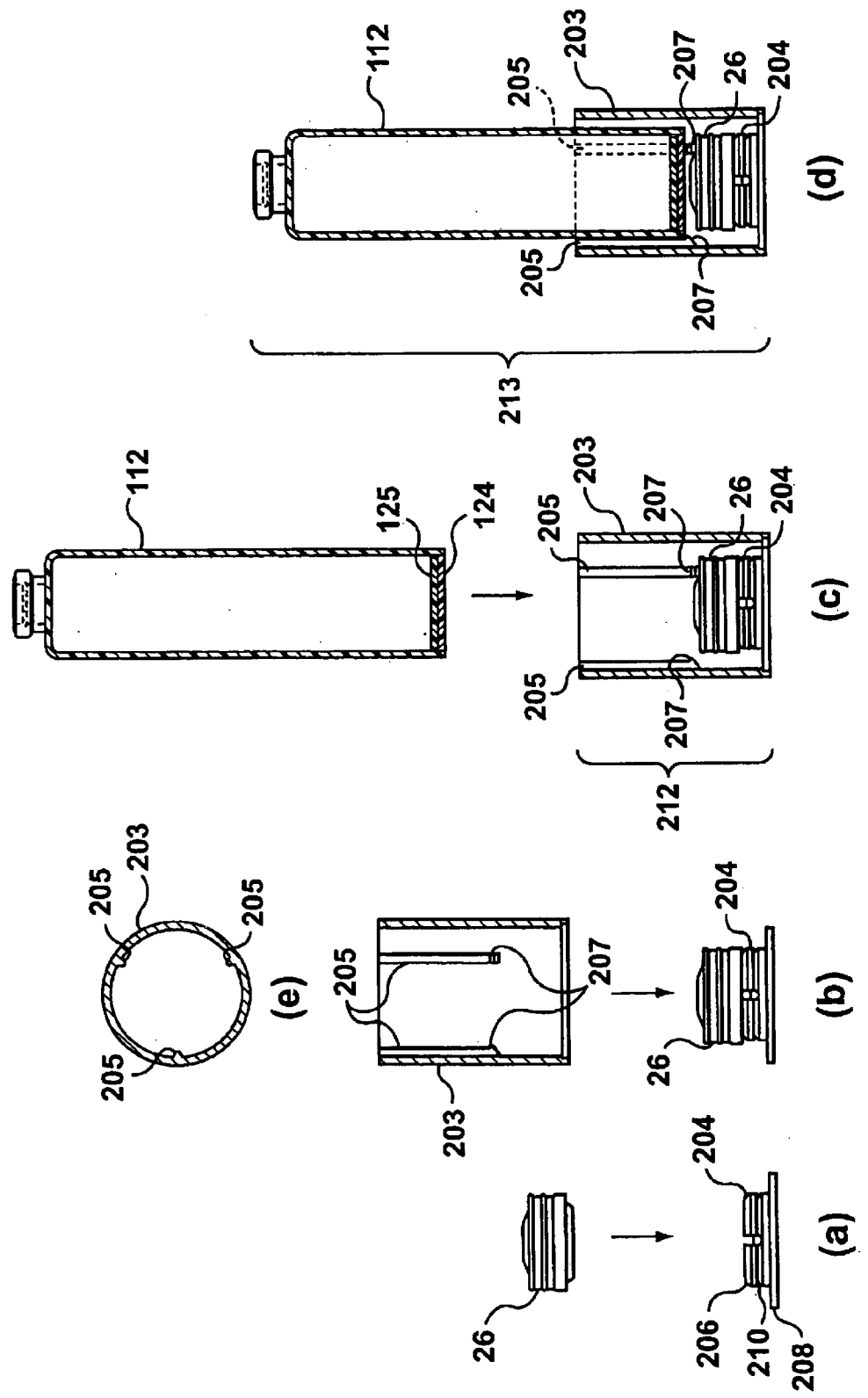
FIG. 13 illustrates a further variant of the syringe barrel according to the second preferred embodiment of the present invention.

A second preferred embodiment of the present invention is now described below with reference to FIG. 8, comprising preparation of a barrel 110 for use in the preparation of a prefilled disposable syringe for administration of a single component medicament. A barrel similar to barrel 10 is shown in FIG. 13 of U.S. Pat. No. 5,137,511, issued on Aug. 11, 1992, commonly assigned to the assignee of the present invention, and incorporated herein by reference in its entirety.

Barrel 110 comprises a body 112 preferably made of glass and having a generally cylindrical side wall 114 with an inner surface 116 and an outer surface 118. At one end, the body 112 has a relatively narrow neck 120 with a neck flange 121 surrounding an open mouth 122, and at the other end the body 112 has an open rimmed end 124. Preferably. the rimmed end 124 is provided with an inwardly extending projection 125 which has a function to be described below. The dimensions of body 112 are similar to those of body 12 described above, although it will be appreciated that the dimensions of body 112 can be varied as discussed above in the context of the first preferred embodiment.

Barrel 110 further comprises a generally cylindrical elastomeric piston 126 having an upper surface 128 which forms the bottom wall of barrel 110 in its assembled state, and an opposed lower surface 130. Piston 126 also has a side surface 132 connecting the upper and lower surfaces 128 and 130, the side surface 132 being adapted to form a hermetic seal with the inner surface 116 of body 112, and preferably being provided with one or more ribs 134 to improve the seal with the body 112. Piston 126 is preferably made from an elastomeric material such as rubber. The lower surface of piston 126 comprises an extension 139 for attachment to a plunger as described in greater detail in above-mentioned European Patent No. 298,585.

The open neck 120 of body 112 is sealed in a conventional manner by an elastomeric closure 136 with an overlying metal cap 138 crimped over the neck flange 121.

The barrel 110 further comprises a stabilization cap 140 which has a number of functions. Firstly, stabilization cap 140 functions as a piston support means, having a cylindrical portion 142 with an upper end 144 and a lower end 146, the upper end having a piston support surface 148. The outer diameter of the cylindrical portion 142 is such that the cylindrical portion 142 can be received inside the body 112. The stabilization cap 140 also has a radially projecting flange 150 at its lower end which functions as a finger flange during use of the syringe. Furthermore, the cylindrical portion 142 of cap 140 has a radially inwardly recessed band 152 which is adapted to form a snap fit with the inwardly projecting portion 125 of the body side wall 114, thereby preventing removal of piston 126 from the body.

FIG. 8 illustrates the steps involved in assembling and filling a barrel 110 with a liquid component of a medicament. The first step, illustrated in FIG. 8a, comprises placement of the of the piston 126 on top of the piston support surface 148 of the stabilization cap, such that the extension 139 of piston 126 is received inside the cylindrical portion 142, which is of sufficient height that the extension 139 does not contact the surface on which the stabilization cap 140 is supported.

The next step comprises placement of a cylindrical sleeve 154 over the piston 126 and cap 140 as illustrated in FIG. 8b. The cylindrical sleeve 154 performs a function similar to that of sleeve 42 of activation cap 40 described above, namely to add stability to the barrel 110 and to support the body 112 in spaced relation to the piston 126 during initial assembly of the barrel 110 In contrast to sleeve 42 of cap 40, the cylindrical sleeve 154 does not form part of the barrel 110, but rather is removed after filling and capping of the barrel 110 on standard equipment for filling and capping pharmaceutical vials. As with sleeve 42, the cylindrical sleeve 154 can further enhance stability of the barrel 110 by being increased in thickness, by providing a flange similar to flange 66 of the cap 40, and/or by forming the sleeve 154 from a relatively dense material, such as stainless steel. Since the sleeve 154 is removed from the barrel, preferably for re-use, forming the sleeve from a relatively thick and/or dense material does not add to the weight or cost of the barrel.

As shown in FIG. 8, it may be preferred to form the sleeve with a partial recess 156 in its lower surface 158 to fit over the flange of the stabilization cap 140, thereby substantially centring the piston 126 within the sleeve 154 and preventing relative movement between the sleeve 154 and the cap 140.

After combining the piston 126, stabilization cap 140 and sleeve 154 to form a first assembly 160 as shown in FIG. 8c, the body 112 is inserted into the top end of the sleeve 154 to form a second assembly 162, with the body 112 being inserted into the sleeve 154 to a sufficient depth that the body 112 is stably supported therein and so that the rimmed end 124 of the body 112 is supported intermediate the top end of sleeve 154 and the flange 150 of the stabilization cap 140.

Preferably, the inner surface of the sleeve 154 is provided with a detent 164 which prevents premature insertion of the piston 126 into the body 112, as discussed in detail with reference to the first preferred embodiment.

The next step of the method, illustrated in FIG. 8d, comprises sterilization of the second assembly 162 by a sterilizing gas. As in the first preferred embodiment, a plurality of assemblies 162 may preferably be packaged in trays with a plastic overwrap prior to sterilization. After sterilization, the piston 126 is inserted into the body 112 by pushing the body 112 downward relative to sleeve in the direction of the arrow shown in FIG. 8e until the inward projection 125 of body 112 snaps into the recess 152 of the stabilization cap.

The steps followed for filling, capping and terminal sterilization of the sealed body 112 are shown in FIGS. 8e to 8i and are identical to the corresponding steps followed in FIGS. 1e to 1i. As with the first preferred embodiment, these steps are performed on standard equipment for filling and capping pharmaceutical vials, with the sealed body 112 and the associated sleeve 154 being conveyed through at least a portion of this equipment while freestanding upright on the finger flange 150.

After removal of the sleeve 154, the barrel 110 can be combined with a needle (not shown) and a plunger (not shown) to form a prefilled disposable syringe, as described in above-mentioned U.S. Pat. No 5,137,511.

FIGS. 9 and 10 illustrate variants of the second preferred embodiment of the invention in which components of the system are attached to trays. In the variant shown in FIG. 9, prefilled syringe barrels 168 are produced by combining a body 12 or 112 with a piston 126 having an extension 139. The barrels 168 include neither an activation cap 40 or a stabilization cap 140 and are therefore similar to pharmaceutical vials, although they may preferably have a greater height to base ratio than standard pharmaceutical vials.

In the variant shown in FIG. 9, a handling tray 170 is provided on which are arranged a plurality of support assemblies 172, each of which comprises a generally cylindrical sleeve 174 having a base end and a top end, and piston support means 176 integrally formed with the sleeve 174 and having an annular piston support surface 178 adapted to support piston 126 by engaging the lower surface 130 thereof. A plan view of tray 170 with support assemblies 172 is shown in FIG. 9d. As in the first embodiment shown in FIGS. 1 to 3, piston support surface 178 is spaced from the inner surface of sleeve by a distance substantially equal to a thickness of the wall of the body 12 or 112 to form an annular gap 180 into which the rimmed end of the body 12 or 112 is received during insertion of the piston 126 into the body 12 or 112.

In order to assemble syringe barrels 168, the pistons 126 are first inserted into support assemblies 172 as shown in FIG. 9a and supported on the piston support means 176. Next, the bodies 12 or 112 are inserted into the sleeves 174 as shown in FIG. 9b and supported therein with their rimmed ends spaced above the upper surfaces 128 of the pistons 126. In order to support the bodies 12 or 112 in the position shown in FIG. 9c, the inner surface of each sleeve 174 is preferably provided with a detent (not shown) as described above in the context of sleeve 42 and 154. After sterilization, the pistons 126 are then inserted into the bodies 12 or 112 by pushing the bodies 12 or 112 downward such that the rimmed ends thereof are pushed down into the gaps 180 (FIGS. 9c and 9e), as described above in connection with the first preferred embodiment illustrated in FIG. 1.

After insertion of the pistons 126, the trays 170 and the barrels 168 are conveyed through equipment which is adapted for filling syringe barrels packaged in trays. After filling, the barrels 168 are sealed and capped as described above, preferably while standing on the trays 170. The filled and capped barrels 168 may then be removed from trays 170 prior to shipment, with the trays being reused. Alternatively, the tray 170 and barrels 168 may be shipped as a unit to their final destination.

FIG. 10 illustrates a variant of the method of FIG. 9, in which trays 182 are provided with piston support means 184 attached thereto. A plan view of the tray is shown in FIG. 10a. As shown in FIGS. 10b and 10c, pistons 139 are placed on the support means. The bodies 12 or 112 are inserted into an assembly 186 comprising a plurality of sleeves 188 joined together, the inner surface of each sleeve 188 having a detent (not shown) to support the rimmed end of the body as shown in FIG. 10d. After insertion of bodies 12 or 112 into sleeves 188 as shown in FIG. 10d, the assembly 186 is placed over the tray 182 so that a piston support means 184 and an associated piston is inserted into each sleeve 188 as shown in FIG. 10e. After sterilization, the pistons 126 are inserted into bodies 12 or 112 as shown in FIG. 10e, thereby providing a tray of sterilized barrels shown in FIG. 10f, ready for filling and capping as described above with reference to FIG. 9.

Figure 11:
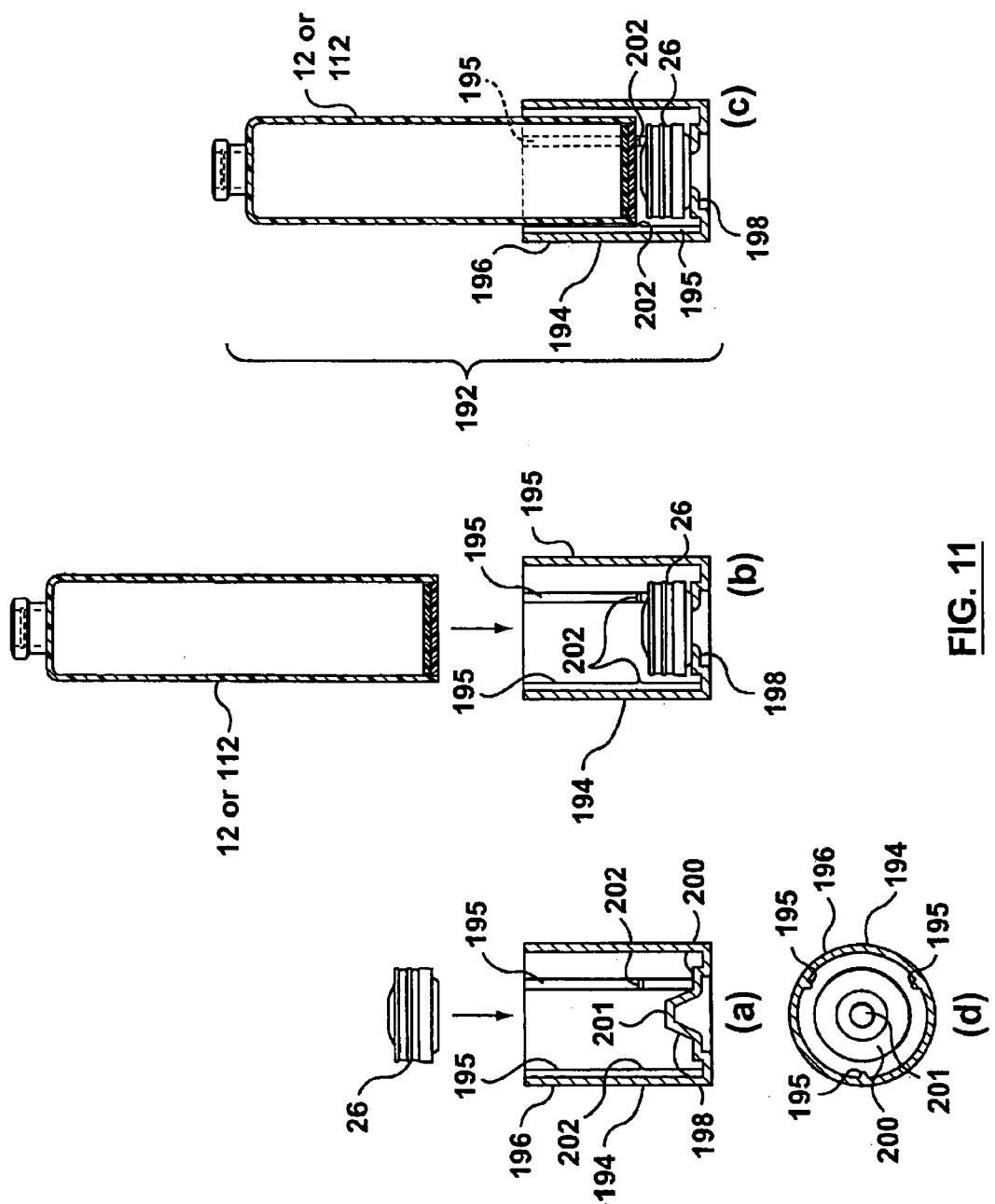
FIG. 11 illustrates a variant of the syringe barrel according to the second preferred embodiment of the present invention.

FIG. 11 illustrates a variant of the second preferred embodiment in which a syringe barrel 192 is produced by combining a body 12 or 112 with a piston 26 having an internally threaded bore. As in the variant shown in FIGS. 9 and 10, the variant of FIG. 11 does not include an activation cap 40 or a stabilization cap 140. In the variant of FIG. 11, the barrel 192 is stabilized on standard equipment for filling and capping vials by a stabilization means 194 comprising a sleeve 196 and an integrally formed piston support means 198 comprising an annular piston support surface 200 and having a raised central portion 201 to be received in the bore of the piston 26, thereby centring the piston inside the sleeve 196. The sleeve 196 is provided with a plurality of axially extending, circumferentially spaced support ribs 195, best seen in FIG. 11d, which is a cross-sectional plan view showing the stabilization means 194 in isolation, the cross-section being taken in a plane perpendicular to the axis of sleeve 196 and between the detents 202 and the piston support means 198. As shown in FIG. 11a, each rib 195 is provided with a detent 202 on its inner surface for supporting the body 12 or 112 above the upper surface 28 of the piston.

To produce a prefilled syringe barrel 192, the piston 26 is first inserted into the stabilization means as shown in FIG. 11a. Next, the body 12 or 112 is inserted into the sleeve 196 as shown in FIG. 11b until the rimmed end engages the detents 202 on ribs 195 as shown in FIG. 11c. It is to be noted that only the stabilization means 194 is shown in cross-section in FIGS. 11a to 11c, with the other components being shown in elevation. The remaining steps are analogous to those shown in FIG. 8, with the exception that, after the barrel 192 is filled and capped, it is pulled out of engagement with the stabilization means 194.

Figure 12:
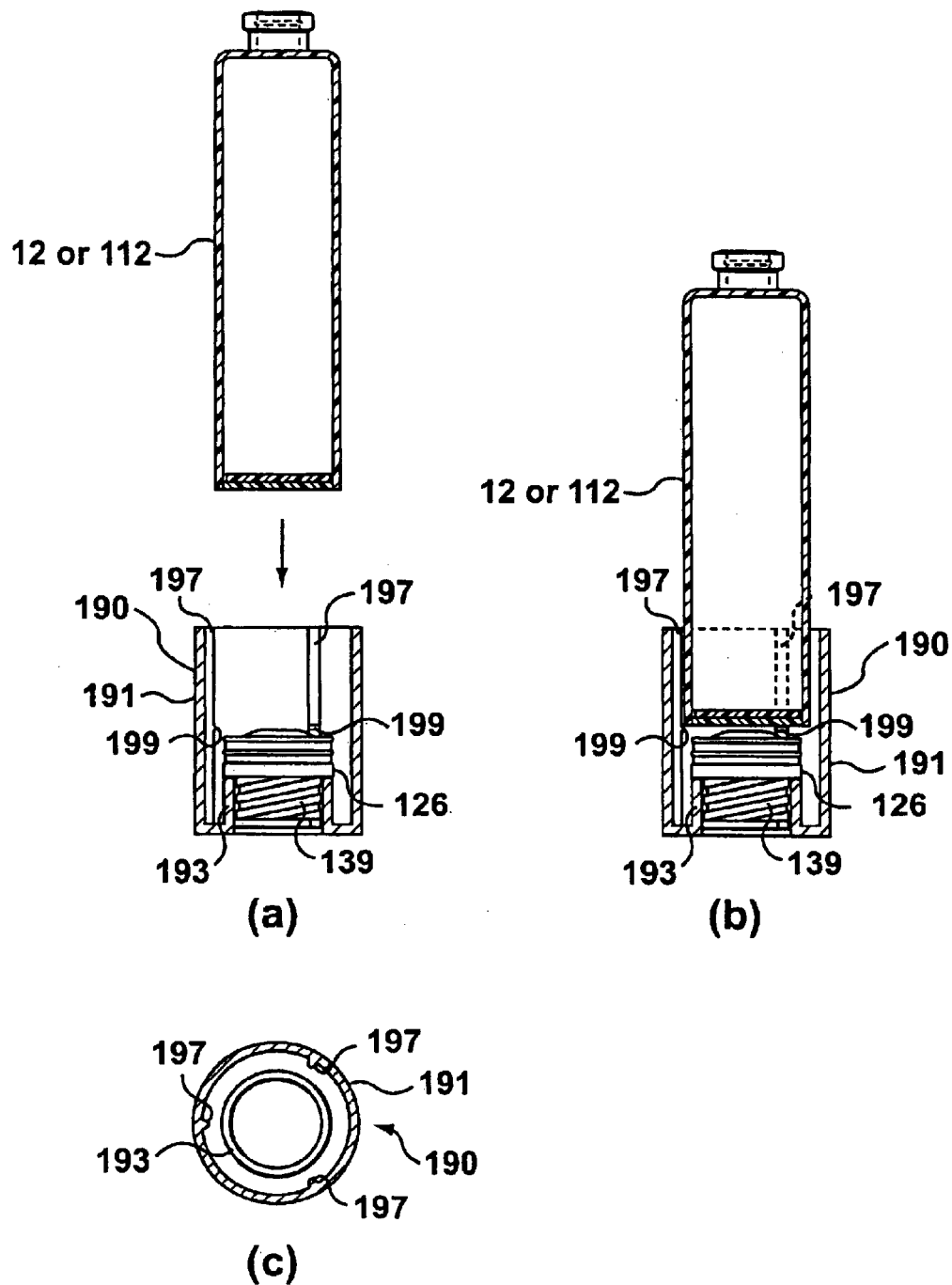
FIG. 12 illustrates a further variant of the syringe barrel according to the second preferred embodiment of the present invention.

FIG. 12 also illustrates a variant of the second preferred embodiment, and is similar to the variant of FIG. 11, with the exception that it is adapted for forming a syringe barrel comprising a body 12 or 112 and a piston 126 having an extension 139. As in FIG. 11, the embodiment of FIG. 12 utilizes a stabilization means 190 comprising a sleeve 191 and a piston support means 193, the sleeve 191 having a plurality of axially extending ribs 197, each of which is provided with a detent 199. FIG. 12a illustrates the subassembly of the piston 126 and the stabilization means 190 prior to insertion of body 12 or 112, FIG. 12b illustrates body 12 or 112 having been inserted into sleeve 191 and being supported by detent 189, such that a gap exists between the rimmed end of the body 12 and the upper surface of piston 126. In FIGS. 12a and 12b, only the stabilization means 190 is shown in cross section, with the other components being shown in elevation. FIG. 12c is a cross-sectional plan view showing the stabilization means in isolation, in a plane which is perpendicular to the axis of sleeve 191, and which is between the detents 199 and piston support means 193.

FIG. 13 illustrates yet another variant of the second preferred embodiment, which is similar to that illustrated in FIG. 8 except that piston 126 is replaced by piston 26 having an internal bore, and sleeve 154 is replaced by sleeve 203, having axially extending ribs 205, each of which is provided with a detent 207. As shown in FIG. 13b, ribs 205 terminate immediately below detents 207. FIG. 13a illustrates piston 26 being placed on stabilization cap 204, comprising a cylindrical portion 206 with a flange 208 at the base end thereof, the flange 208 serving as a finger flange. Stabilization cap 204 also comprises a recessed band 210 adapted to snap into engagement with the inwardly projecting portion 125 at the rimmed end 124 of body 112 FIG. 13b illustrates the placement of the cylindrical sleeve 203 over the piston 26 and the stabilization means 204 to form the assembly 212 shown in FIG. 13c. FIG. 13c also shows insertion of the insertion of body 112 into sleeve 203 to form the assembly 213 shown in FIG. 13d, which is ready for sterilization and further processing according to the method described in connection with FIG. 8. FIGS. 13a to 13d illustrate the sleeve 203 in cross section and the other components in elevation FIG. 13e is a cross-sectional plan view showing the sleeve 203 in isolation, taken in a plane extending through ribs 205 and perpendicular to the axis of sleeve 203.

FIG. 14 illustrates a variant of the first preferred embodiment of the present invention, identical to that shown in FIGS. 1 to 3 except that syringe body 12 is replaced by body 214 having a rimmed edge 216 with slight outward projection 218 and a slight inward projection 220. FIG. 14a is analogous to FIG. 2 and illustrates an assembly comprising the body 214, plunger 26 and activation cap 40 prior to insertion of piston 26 into body 214 FIG. 14b is analogous to FIG. 3 and illustrates the assembly of FIG. 14a after the body 214 has been pushed down into activation cap 40, and piston 26 is inserted into body 214.

It will be appreciated that the activation caps, stabilization caps, sleeves and handling trays described above will preferably be made from materials which are substantially unaffected by the conditions employed during sterilization. As sterilization is usually performed at elevated temperature, it is preferred that these components be made of heat-resistant materials. It is preferred that these components be formed from plastics, more preferably heat-resistant plastics.

Furthermore, it may be preferred in some embodiments of the present invention to utilize syringe bodies and pistons which are siliconized. Siliconization is preferably performed during manufacture of the syringe body and the piston.

Although the invention has been described with reference to certain preferred embodiments, it is not limited thereto. Rather, the invention includes all embodiments which may fall within the scope of the following claims.

What is claimed is:

1. An assembly for forming a barrel of a pre-filled syringe, comprising:
   (a) a syringe body having a generally cylindrical side wall with an inner surface and an outer surface, the side wall extending between a lower rimmed end and an upper neck end;
   (b) a generally cylindrical elastomeric piston having an upper surface, a lower surface and a side surface;
   (c) a generally cylindrical sleeve having a base end and a top end, wherein said syringe body is received inside the top end of the sleeve intermediate the top end and the base end of the sleeve; said sleeve being in a close fit with the rimmed end of the syringe body;

(d) piston support means integrally formed with the sleeve, said piston support means having a support surface on which the piston is supported, said lower surface of said piston proximate to and engaging said piston support means and said upper surface of said piston distally located with respect to said piston support means, said upper surface of said piston being spaced longitudinally apart from the rimmed end of the syringe body, said piston residing outside said syringe body while the syringe body is receive inside the top end of the sleeve thereby creating a gap between the upper surface of the piston and the rimmed end of the syringe body, permitting sterilization of the syringe body and the piston by a sterilizing gas; and (e) said side surface of said piston adapted to form a hermetic seal with the inner surface of the cylindrical side wall of said syringe body when said piston is inserted into the rimmed end of the syringe body after sterilization.

2. The assembly of claim 1, wherein the base end of the sleeve has an outer diameter sufficient to permit the assembly to be conveyed standing upright through an apparatus for filling and capping pharmaceutical vials.

3. The assembly of claim 1, wherein the base end of the sleeve has an outwardly projecting flange, the flange having a diameter and a height so as to prevent interference such as would cause tipping when the assembly is conveyed standing upright through an apparatus for filling and capping pharmaceutical vials.

4. The assembly of claim 3, wherein the flange has a substantially flat radially outwardly facing wall which is substantially vertical when the assembly is standing upright.

5. The assembly of claim 1, wherein the sleeve has an inwardly projecting portion intermediate the base end and the top end for supporting the rimmed end of the syringe body.

6. The assembly of claim 5, wherein the inwardly projecting portion comprises a detent of sufficient shape and size to retain the rimmed end of the syringe body intermediate the top end and the base end of the sleeve in the absence of a force which pushes the rimmed end of the syringe body and the base end of the sleeve toward one another, but which permits the rimmed end and the base end to be pushed toward one another in response to a predetermined force.

7. The assembly of claim 1, wherein the piston support means comprises a piston support surface located radially inwardly of the inner surface of the syringe body side wall.

8. The assembly of claim 7, wherein the piston support surface is annular with a central aperture through which the piston can be engaged by a plunger.

9. The assembly of claim 8, wherein the piston support surface is positioned relative to the base end of the sleeve such that the piston is supported above the base end of the sleeve when the assembly is standing upright.

10. The assembly of claim 9, wherein the piston support surface is spaced inwardly from the inner surface of the sleeve by a distance substantially equal to a thickness of the syringe body side wall, thereby forming an annular recess between the piston support surface and the inner surface of the sleeve, the annular recess having a bottom wall intermediate the piston support surface and the lower surface of the base end, such that when a force is applied to push the rimmed end of the syringe body into the annular recess until it engages the bottom wall, the piston becomes fully inserted in the syringe body with its side surface forming a hermetic seal with the syringe body side wall.

11. The assembly of claim 1, wherein the piston support means comprises a stabilization cap comprising a hollow cylindrical portion with an upper end and a lower end adapted to fit inside the syringe body, with the upper end of the cylindrical portion forming a piston support surface for engagement with the lower surface of the piston, the stabilization cap further comprising a finger flange projecting radially outwardly at the lower end of the adapter ring.

12. The assembly of claim 11, wherein the finger flange fits inside the base end of the sleeve.

13. The assembly of claim 1, wherein a plurality of said piston support means are arranged on a tray.

14. The assembly of claim 7, wherein a plurality of said integrally formed sleeves and piston support means are arranged on a tray.

15. A pre-filled syringe, comprising:

(a) a syringe body having a generally cylindrical side wall with an inner surface and an outer surface, the side wall extending between a lower rimmed end and an upper neck end;

(b) a generally cylindrical elastomeric piston having an upper surface, a lower surface and a side surface;

(c) a generally cylindrical sleeve having a base end and a top end, wherein said syringe body is received inside the top end of the sleeve intermediate the top end and the base end of the sleeve; said sleeve being in a close fit with the rimmed end of the syringe body;

(d) said sleeve includes a piston support surface on which said piston is supported, said lower surface of said piston proximate to and engaging said piston support surface and said upper surface of said piston distally located with respect to said piston support surface, said upper surface of said piston being spaced longitudinally apart from said rimmed end of said syringe body, said piston residing outside said syringe body while the syringe body is receive inside the top end of the sleeve thereby creating a gap between said upper surface of said piston and said rimmed end of said syringe body permitting sterilization of said syringe body and said piston by a sterilizing gas; and (e) said side surface of said piston adapted to form a hermetic seal with the inner surface of the cylindrical side wall of said syringe body when said piston is inserted into the rimmed end of the syringe body after sterilization.

* * * * *

UNITED STATES PATENT AND TRADEMARK OFFICE
CERTIFICATE OF CORRECTION

PATENT NO.    : 6,802,828 B2
DATED         : October 12, 2004
INVENTOR(S)   : Reynolds It is certified that error appears in the above-identified patent and that said Letters Patent is hereby corrected as shown below:

Column 13,
Line 12, delete "receive" and insert -- received -- and

Column 14,
Line 48, delete "receive" and insert -- received --.

Signed and Sealed this

Fifteenth Day of February, 2005

JON W. DUDAS
*Director of the United States Patent and Trademark Office*